(12) United States Patent
Lelandais

(10) Patent No.: US 6,559,109 B2
(45) Date of Patent: May 6, 2003

(54) 1,3-OXATHIANES AS PERFUMING AND FLAVORING INGREDIENTS

(75) Inventor: Patrick Lelandais, Saint Julien en Genevois (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/053,324

(22) Filed: Jan. 17, 2002

(65) Prior Publication Data
US 2002/0155960 A1 Oct. 24, 2002

(30) Foreign Application Priority Data
Feb. 1, 2001 (WO) .............................. PCT/IB01/00126

(51) Int. Cl.$^7$ .......................... C11D 3/50; A61K 7/46; C07D 327/06
(52) U.S. Cl. .......................... 510/103; 512/12; 549/14
(58) Field of Search .......................... 549/14; 510/103; 512/12

(56) References Cited

U.S. PATENT DOCUMENTS 4,220,561 A 9/1980 Winter et al. ................ 252/522

OTHER PUBLICATIONS

K. Nishide et al, "A Novel Tandem [4$^+$+2] Cycloaddition–elimination Reaction of 4,4–Dimethyl–2–Styryl–1,3–Oxathianes with Olefins", Tetrahedron Letters 41, pp. 371–375 (2000).

K. Pihlaja, "Conformational Analysis", XIX† Properties and Reactions of 1,3–Oxathianes VIII§ A$^1$H NMR Conformational Study of Methyl–Substituted Derivatives, Organic Magnetic Resonance, vol. 12, No. 5 pp. 331–336 (1979).

N. de. Wolf, "Conformation of Non–Aromatic Ring Compounds, Part 62(1) NMR Spectra and Geometry of Some 1,3–Oxathianes", Tetrahedron Letters No. 8, pp. 551–554 (1970).

*Primary Examiner*—John R Hardee
(74) *Attorney, Agent, or Firm*—Winston & Strawn

(57) ABSTRACT

The present invention relates to the perfumery and flavor industry. It concerns more particularly the use of a compound of formula (I) as perfuming or flavoring ingredient

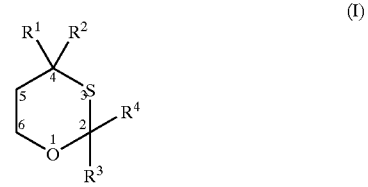

wherein $R^1$ and $R^2$ represent simultaneously or a independently a linear or branched alkyl or alkenyl group containing 1 to 4 carbon atoms, $R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R^4$ represents a hydrogen or a linear alkyl group containing 1 to 4 carbon atoms.

Substituents groups of $R^3$ can be for example $C_1$–$C_3$ alkyl or alkenyl groups, an aromatic ring or $C_5$–$C_7$ cycloalkyl or cycloalkenyl groups, possibly substituted by methyl or ethyl groups.

17 Claims, No Drawings

1,3-OXATHIANES AS PERFUMING AND FLAVORING INGREDIENTS

TECHNICAL FIELD

The present invention relates to the perfumery and flavor industry. It concerns more particularly the use of a compound of formula (I) as perfuming or flavoring ingredient

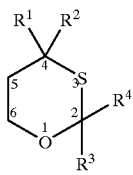

(I)

wherein $R^1$ and $R^2$ represent simultaneously or independently a linear or branched alkyl or alkenyl group containing 1 to 4 carbon atoms;

$R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R^4$ represents a hydrogen or a linear alkyl group containing 1 to 4 carbon atoms.

Substituents groups of $R^3$ can be for example $C_1$–$C_3$ alkyl or alkenyl groups, an aromatic ring or $C_5$–$C_7$ cycloalkyl or cycloalkenyl groups, possibly substituted by methyl or ethyl groups.

PRIOR ART

Many 1,3-oxathianes and their use in the flavor and fragrance industry have been investigated for several years. The best known amongst these is 2-methyl-4-propyl-1,3-oxathiane, described in U.S. Pat. No. 4,220,561, which is very much appreciated in the flavoring industry for it sweet, passion fruit note.

Up to now, all the 1,3-oxathianes reported in the prior art and known to be useful in the perfuming or flavoring industry are mono substituted in position 4 of the ring or, at least, they carry a substituent in position 5 or 6 of the ring.

To the best of our knowledge, there are only six compounds of formula (I) reported in the prior art but no odor or flavor properties have been reported for any of them. *Tetrahedron Lett.*, 2000, 41, 371–5 teaches the use of 2-[2-(4-methoxy-phenyl)ethenyl]-4,4-dimethyl-1,3-oxathiane and 4,4-dimethyl-2-(2-phenylethenyl)-1,3-oxathiane as chemical intermediates in cycloaddition-elimination reactions. *Org. Magn. Reson.*, 1979, 12, 331–6 and *Tetrahedron Lett.*, 1970, 8, 551–4 report studies on the cycle conformation of 2,2,4,4-tetramethyl-1,3-oxathiane, 2,4,4-trimethyl-1,3-oxathiane and 4,4-dimethyl-1,3-oxathiane. Finally, 2-(2-methyl-1-propenyl)-4,4-dimethyl-1,3-oxathiane is known only as a Chemical Abstract registry number, but is not described in the literature.

DESCRIPTION OF THE INVENTION

Surprisingly, we have now been able to establish that the compounds of formula

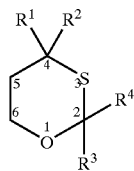

(I)

as defined above, possess useful and surprising organoleptic properties, which render them very convenient for the perfume and flavor industry.

Preferred compounds of formula (I) are those of formula

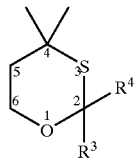

(II)

wherein $R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R^4$ represents a hydrogen or a methyl group.

Substituents groups of $R^3$ can be for example $C_1$–$C_3$ alkyl or alkenyl groups, an aromatic ring or $C_5$–$C_7$ cycloalkyl or cycloalkenyl groups, possibly substituted by methyl or ethyl groups.

The odor and flavor properties of compounds of the invention appear as totally unexpected in view of the prior art with is totally silent with regard to the organoleptic behavior of their analogues.

The odor profile of the compounds of formula (II) appears to depend on the nature of the substituents $R^3$ and $R^4$. Frequently, the odor profile is of the herbaceous and sulfury type, in association with notes of the fruity, minty or aromatic herbs type. In other instances, the odor profile is of the sulfury type with notes of the animal/perspiration, woody, green or fruity type. Some compounds present odors of the herbaceous type, together with fruity, aromatic herbs type notes, or yet herbaceous or sulfury notes, together with fruity or aromatic herbs nuances.

Amongst the compounds of formula (II), 2-heptyl-4,4-dimethyl-1,3-oxathiane (odor profile: cassis, fruity, lemon, green, natural), 2-(5-methyl-2-furyl)-4,4-dimethyl-1,3-oxathiane (odor profile: cassis, herbaceous, sulfury, with exotic fruit, cassis, natural bottom notes), 4,4-dimethyl-2-propyl-1,3-oxathiane (odor profile: herbaceous-aromatic, parsley, thujonic, slightly lime and sulfury-buchu character) and 2,4,4-trimethyl-2-penthyl-1,3-oxathiane (odor profile: sweet, sugary, slightly onion but very natural, basil leaves, with basil, sage, tagetes, sulfury and natural bottom notes) are very much appreciated for their original odor profile.

Even more preferred are the 2-ethyl-4,4-dimethyl-1,3-oxathiane and 2-(2,4-dimethyl-3-cyclohexene-1-yl)-4,4-dimethyl-1,3-oxathiane. 2-Ethyl-4,4-dimethyl-1,3-oxathiane has an odor profile of the type herbaceous, sage, tagete leaves, cassis, wild mint, slightly sulfury type with an onion under note. This is a very natural and outstanding perfuming ingredient, possessing an unusual green, thyme note that adds a natural touch to the herbaceous note when used in compositions at low proportions.

2-(2,4-Dimethyl-3-cyclohexene-1-yl)-4,4-dimethyl-1,3-oxathiane has a multiodorant profile comprising green, natural, herbaceous, chervil, artemisia, tagete, sage nuances, is also very natural and confers to the herbaceous-aromatic compositions an improved impact and a very natural aspect, even at low concentrations.

The compounds of the invention can be used in a wide range of concentrations to create fragrance effects totally unexpected heretofore. The compounds of the invention can suit almost all the fields of modern perfumery. One can cite the applications in fine perfumery, namely in the creation of perfumes and colognes, wherein novel and original odor effects can be obtained.

The compounds of the invention can also be used in functional perfumery, namely to perfumed soaps, shower or bath gels, shampoos, body deodorants and antiperspirants, ambient air deodorants, liquid or solid detergents for textile treatment, detergent compositions or cleaning products for dishes or varied surfaces, or cosmetic preparations.

In these applications, the compounds according to the invention can be used alone, as well as mixed with other perfuming ingredients, solvents or additives commonly used in perfumery. The nature and variety of these co-ingredients do not require a more detailed description here, which would not be exhaustive anyway. In fact, a person skilled in the art, having a general knowledge, is able to choose them according to the nature of the product that has to be perfumed and the olfactory effect sought. These perfuming co-ingredients belong to varied chemical groups such as alcohols, aldehydes, ketones, esters, ethers, acetates, nitriles, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books, or yet in the specialized patent literature commonly available in the art.

The proportions in which the compounds according to the invention can be incorporated in the different products mentioned above vary in a broad range of values. These values depend on the nature of the product that has to be perfumed and on the olfactory effect sought, as well as on the nature of the co-ingredients in a given composition when the compounds of the invention are used in admixture with perfuming co-ingredients, solvents or additives commonly used in the art.

In a general manner, the compounds according to the invention will be used in small amounts, typically at high dilution, owing to their strong odor impact.

For instance, concentrations from 0.01% to 5%, and preferably from 0.02% to 3%, by weight of these compounds, with respect to the perfuming composition in which they are incorporated, can be typically used. Much lower concentrations than these can be used when these compounds are directly applied for perfuming some of the consumer products mentioned above.

As previously mentioned, the compounds of the invention are also useful in the field of flavors, i.e. to impart taste to flavoring compositions and foods or beverages for example.

Their taste, which appears to be a function of the nature of the $R^3$ and $R^4$ groups, is generally of the herbal, hop type, in association with fatty or floral notes. Occasionally, woody, terpenic type notes together with spicy or fruity notes characterize the taste of some of the compounds of the invention. In particular the taste of 4,4-dimethyl-2-propyl-1,3-oxathiane is of the woody, terpenic, pepper type whereas 4,4-dimethyl-2-(1-methylbutyl)-1,3-oxathiane presents a terpenic, woody, black-currant, grapefruit flavor and 2-(2,4,4-trimethyl-1,3-oxathiane-2-yl)-acetamide possesses a herbal, hop, beer, sulfury type flavor.

In flavor applications, the compounds according to the invention will typically be used in concentrations of the order of 0.1 to 10 ppm with respect to the product into which they are incorporated. Much higher concentrations can be chosen when the compounds are used in concentrated flavors or flavoring compositions, intended to be incorporated in consumer products.

The compounds of the invention thus make it possible to confer, improve, enhance or modify the odor or taste of a consumer product, as well as of perfuming bases or concentrates, or yet flavor preparations and compositions.

The invention will now be described in further detail by way of the following examples, wherein the abbreviations have the usual meaning in the art and the temperatures are indicated in degrees centigrade (° C.). The NMR spectral data were recorded with a 360 MHz machine in $CDCl_3$, chemical displacements δ being indicated in ppm with respect to the TMS as standard, and the coupling constant J being expressed in Hz. All the starting aldehydes are commercially available unless otherwise specified. 3-Methyl-3-mercapto-butanol was obtained according to B. J. Sweetman et al., *J. Med. Chem.*, (1971), 14, 868.

EXAMPLE 1

General Procedure for the Preparation of the Compounds of Formula (II)

To a solution of 3-methyl-3-mercapto-butanol (0.1 mole) and paratoluenesulfonic acid monohydrate (0.0015 mole) in diisopropyl ether (80 ml), there was added over 15 min the required aldehyde or ketone (0.1 mole) (according to Table 1). Reactions involving aldehydes or ketones having a boiling point lower than 80° C. were carried out in dichloromethane.

The mixture is then heated to reflux with azeotropic removal of water until no conversion is observed any longer (GC). After cooling to room temperature, the reaction mixture is washed with 10% aqueous sodium hydroxide (3×), then with brine to neutrality. The final oxathiane was obtained after concentration of the solvent (rotary evaporator) followed by bulb-to-bulb distillation under vacuum.

Tables 1 and 2 summarize the compounds that were thus obtained, as well as their organoleptic properties and physical data.

TABLE 1

| Compound structure Name | Odor profile | Starting aldehyde | Physical data |
|---|---|---|---|
| 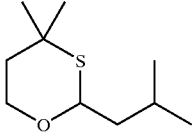<br>2-isobutyl-4,4-dimethyl-1,3-oxathiane | herbaceous, thyme, phenolic, lemon | 3-methylbutanal | MS: 188($M^+$, 14), 131(100), 102(8), 87(19), 69(92), 59(23), 41(48) |
| 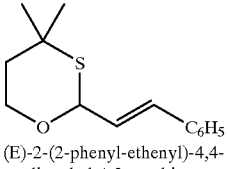<br>(E)-2-(2-phenyl-ethenyl)-4,4-dimethyl-1,3-oxathiane | sulfury, oily, animal, coffee | 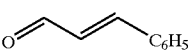 | MS: 234($M^+$, 100), 165(8), 147(25), 133(22), 131(38), 115(25), 104(31), 87(15), 69(20), 59(10), 55(8), 41(8) |
| 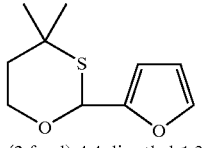<br>2-(2-furyl)-4,4-dimethyl-1,3-oxathiane | sulfury, cassis, box-tree, herbaceous | furfural | MS: 198($M^+$, 100), 112(25), 102(83), 97(48), 95(22), 87(31), 74(23), 69(32), 59(20), 56(18), 41(17) |
| 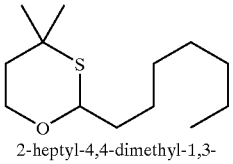<br>2-heptyl-4,4-dimethyl-1,3-oxathiane | cassis, fruity, lemon, green, natural | octan-1-al | MS: 230($M^+$, 10), 131(100), 102(8), 87(9), 69(37), 41(8)<br>$^1$H-NMR: 0.87 (t, J = 7, 3H, $CH_3$(7')); 1.28 (s, 3H, $CH_3$); 1.22–1.32 (br. m, 8 H, 4 $CH_2$); 1.43 (dt, J = 13 and 2, 1H, Heq-C(5)); 1.48 (s, 3H, $CH_3$); 1.40–1.82 (m, 4H, $CH_2$(1' and 2')); 1.88 (td, J = 13 and 4.5, 1H, Hax-C(5)); 3.75 (td, J = 13 and 2, 1H, Hax-C(6)); 4.04 (ddd, J = 13, 4.5, and 2, 1H, Heq-C(6)); 4.78 (dd, J = 7 and 5, 1H, H-C(2)). |
| 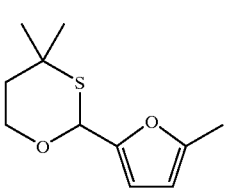<br>2-(5-methyl-2-furyl)-4,4-dimethyl-1,3-oxathiane | cassis, herbaceous, sulfury-oxane, with exotic fruit, cassis, natural bottom notes | 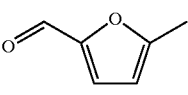 | MS: 212($M^+$, 100), 137(9), 126(30), 111(100), 102(51), 95(9), 87(21), 74(15), 69(23), 59(12), 41(10)<br>$^1$H-NMR: 1.33 (s, 3H, $CH_3$); 1.48 (dt, J = 13 and 2, 1H, Heq-C(5)); 1.55 (s, 3H, $CH_3$); 2.03 (td, J = 13 and 4.5, 1H, Hax-C(5)); 2.28 (s, 3H, $CH_3$—C(5')); 3.93 (td, J = 13 and 2, 1H, Hax-C(6)); 4.16 (ddd, J = 13, 4.5, and 2, 1H, Heq-C(6)); 5.84 (s, 1H, H-C(2)); 5.92 (m, 1H, HC(4')); 6.32 (d, J = 3, 1H, HC(3')). |
| 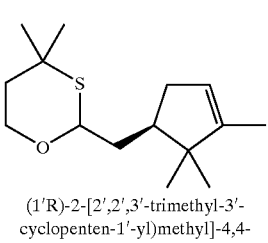<br>(1'R)-2-[2',2',3'-trimethyl-3'-cyclopenten-1'-yl)methyl]-4,4-dimethyl-1,3-oxathiane | sulfury, box-tree, sage, perspiration | <br>(ref.: J. A. Bajgrowicz et al, Helv. Chem.Acta (1998), 81, 1349) | MS: 254($M^+$, 18), 221(11), 185(25), 131(8), 108(100, 93(32), 69(25), 41(12) |

TABLE 1-continued

| Compound structure Name | Odor profile | Starting aldehyde | Physical data |
|---|---|---|---|
| 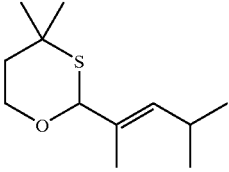<br>(E)-2-(1,3-dimethyl-1-butenyl)-4,4-dimethyl-1,3-oxathiane | herbaceous, aromatic, cassis, passion fruit | 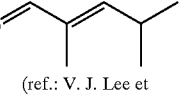<br>(ref.: V. J. Lee et al, J.Am.Chem. Soc.(1978), 100, 4225) | MS: 214($M^+$, 100), 171(87), 145(8), 131(25), 112(64), 102(67), 97(18), 95(28), 87(45), 74(30), 69(95), 59(30), 55(35), 41(48) |
| 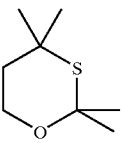<br>2,2,4,4-tetramethyl-1,3-oxathiane | herbaceous, thujone, minty, camphoraceous | acetone | MS: 160($M^+$, 30), 145(28), 102(55), 87(40), 74(61), 69(72), 59(100), 56(48), 43(40), 41(72) |
| 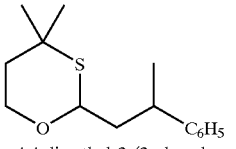<br>4,4-dimethyl-2-(2-phenyl-propyl)-1,3-oxathiane | green, sulfury, isocyclocitral, Triplat | 3-phenyl-butanal | MS: 250($M^+$, 48), 172(31), 147(8), 145(18), 131(100), 130(90), 105(68), 91(25), 77(21), 69(70), 59(15), 55(9), 41(20) |
| 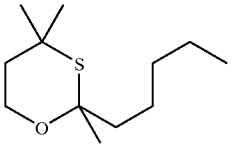<br>2,4,4-trimethyl-2-penthyl-1,3-oxathiane | sweet, sugary, slightly onion but very natural, basil leaves, with basil, sage, tagete, sulfury and natural bottom notes | methyl-pentyl ketone | MS: 216($M^+$, 5), 201(8), 145(100), 115(5), 102(35), 87(20), 74(18), 69(40), 59(12), 56(10), 55(10), 41(15)<br>$^1$H-NMR: 0.89 (t, J = 7, 3H, $CH_3(5')$); 1.37 (s, 3H, $CH_3$); 1.22–1.48 (br. m, 6 H, 3 $CH_2$); 1.40 (s, 3H, $CH_3$); 1.57 (s, 3H, $CH_3$—C(2)); 1.66 (m, 2H, $CH_2(5)$); 1.83 (m, 2H, $CH_2$ (1')); 3.92 (m, 2H, $CH_2(6)$). |
| 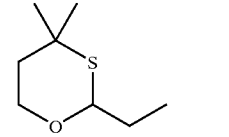<br>2-ethyl-4,4-dimethyl-1,3-oxathiane | herbaceous, sage, tagete, cassis, wild mint, slightly sulfury with an onion under note | propan-1-al | MS: 160($M^+$, 42), 131(100), 87(18), 74(21), 69(72), 59(18), 56(14), 41(20)<br>$^1$H-NMR: 1.00 (t, J = 7, 3H, $CH_3$—$CH_2$); 1.28 (s, 3H, $CH_3$); 1.43 (dt, J = 13 and 2, 1H, Heq-C(5)); 1.48 (s, 3H, $CH_3$); 1.62–1.82 (m, 2H, $CH_3$—CH2); 1.89 (td, J = 13 and 4.5, 1H, Hax-C(5)); 3.77 (td, J = 13 and 2, 1H, Hax-C(6)); 4.05 (ddd, J = 13, 4.5, and 2, 1H, Heq-C(6)); 4.73 (t, J = 6, 1H, H-C(2)).<br>$^{13}$C-NMR: 10.0 (q, $CH_3$—$CH_2$); 26.9 (q, $CH_3$); 29.0 (t, $CH_3$—$CH_2$); 32.5 (q, $CH_3$); 39.7 (t, $CH_2(5)$); 40.0 (s, C(4)); 65.9 (t, $CH_2(6)$); 81.1 (d, CH(2)). |
| 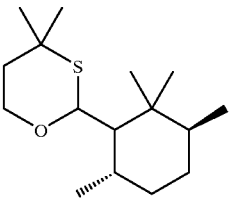<br>4,4-dimethyl-2-(2,2,r-3,t-6-tetramethyl-1-cyclo-hexyl)-1,3-oxathiane | woody, sulfury, buchu, sage, tropical fruit | 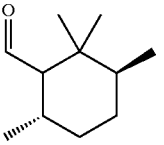<br>(ref.: C. Chapuis et al, Helv.Chem.Acta (1193), 76, 2070) | MS: 270($M^+$, 12), 131(100), 69(40), 55(10), 41(14) |

TABLE 1-continued

| Compound structure Name | Odor profile | Starting aldehyde | Physical data |
|---|---|---|---|
| 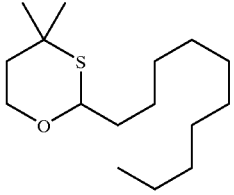<br>2-decyl-4,4-dimethyl-1,3-oxathiane | herbaceous, tagete, sulfury, cress, match, cassis, tagetone | undecan-1-al | MS: 272(M$^+$, 8), 152(4), 131(100), 102(6), 87(8), 69(38), 55(8), 41(12) |
| 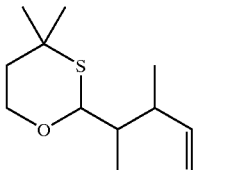<br>4,4-dimethyl-2-(2,4,6-trimethyl-3-cyclohene-1-yl)-1,3-oxathiane | herbaceous, green, sulfury, pyrogenous | 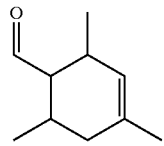 | MS: 254(M$^+$, 38), 185(78), 167(41), 134(58), 131(95), 123(32), 121(27), 107(18), 69(100), 59(8), 55(10), 41(27) |
| 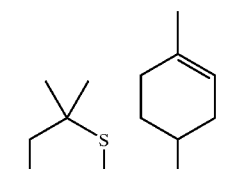<br>4,4-dimethyl-2-[2-(4-methyl-3-cyclohexen-1-yl)propyl]-1,3-oxathiane | herbaceous, sulfury, chervil, artemisia, sage, cassis, green, mint leaves, very natural | 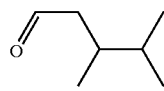 | MS: 268(M$^+$, 5), 181(22), 171(31), 149(20, 148(100), 133(48), 93(25), 69(50), 59(8), 55(15), 41(20) |
| 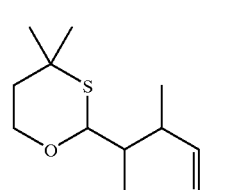<br>2-(2,4-dimethyl-3-cyclohexene-1-yl)-4,4-dimethyl-1,3-oxathiane | green, natural, herbaceous, chervil, artemisia, tagete, sage type | 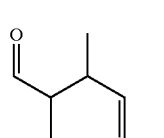<br>(>75% cis and <25% trans) | $^1$H-NMR: (major isomer) 0.88 (d, J = 7.5, 3H, CH$_3$—CH); 1.28 (s, 3H, CH$_3$); 1.27–1.48 (m, 2H); 1.47 (s, 3H, CH$_3$); 1.62 (br. s, 3H, CH$_3$—C=C); 1.80–2.05 (m, 4H); 2.50 (m, 1H, CH$_3$—CH); 3.70 (td, J = 13 and 2, 1H, Hax-C(6)); 4.05 (ddd, J = 13, 4.5, and 2, 1H, Heq-C(6)); 4.67 (d, J = 10, 1H, H-C(2)); 5.36 (m, 1H, C=CH).<br>$^{13}$C-NMR: (major isomer) 15.2 (q, CH$_3$—C(2')); 20.1 (t, CH$_2$(6')); 23.4 (q, CH$_3$—C(4')); 27.1 (q, CH$_3$—C(4)); 30.0 (d, CH(2')); 30.5 (t, CH$_2$(5')); 32.7 (q, CH$_3$—C(4')); 39.7 (s, C(4)); 39.9 (t, CH$_2$(5)); 42.7 (d, CH(1')); 65.9 (t, CH$_2$(6)); 82.3 (d, CH(2)); 127.3 (d, CH(3')); 132.6 (s, C(4')). |
| 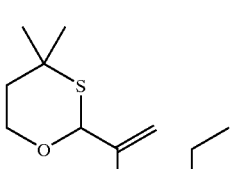<br>4,4-dimethyl-2-(1-pentyl-ethenyl-1,3-oxathiane | herbaceous, sulfury, basil, parsey, chervil, verbena, citrus, eldet, minty, slightly sulfury-onions, very natural | 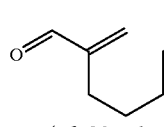<br>(ref.: Marvel et al. J.Am. Chem.Soc. (1948), 70, 1698) | MS: 228(M$^+$,45), 195(8), 171(15), 159(10), 157(18), 131(36), 126(60), 102(52), 87(42), 74(30), 69(100), 59(25), 55(29), 41(42) |

TABLE 1-continued

| Compound structure Name | Odor profile | Starting aldehyde | Physical data |
|---|---|---|---|
| 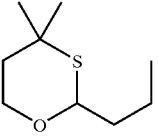 4,4-dimethyl-2-propyl-1,3-oxathiane | herbaceous-aromatic, parsley, thujonic, slightly lime and sulfury-buchu | butan-1-al | MS: 174(M$^+$, 18), 131(100), 87(20), 74(16), 69(95), 59(28), 55(18), 41(38)<br>$^1$H-NMR: 0.92 (t, J = 7, 3H, CH$_3$(3')); 1.28 (s, 3H, CH$_3$); 1.43 (dt, J = 13 and 2, 1H, Heq-C(5)); 1.48 (s, 3H, CH$_3$); 1.40–1.82 (m, 4H, CH$_2$(1' and 2')); 1.88 (td, J = 13 and 4.5, 1H, Hax-C(5)); 3.75 (td, J = 13 and 2, 1H, Hax-C(6)); 4.04 (ddd, J = 13, 4.5, and 2, 1H, Heq-C(6)); 4.80 (dd, J = 7 and 5, 1H, H-C(2)). |

TABLE 2

| Compound structure Name | Flavor profile | Starting aldehyde | Physical data |
|---|---|---|---|
| 4,4-dimethyl-2-propyl-1,3-oxathiane | woody, terpeny, pepper | butan-1-al | MS: 174(M$^+$, 18), 131(100), 87(20), 74(16), 69(95), 59(28), 55(18), 41(38)<br>$^1$H-NMR: 0.92 (t, J = 7, 3H, CH$_3$(3')); 1.28 (s, 3H, CH$_3$); 1.43 (dt, J = 13 and 2, 1H, Heq-C(5)); 1.48 (s, 3H, CH$_3$); 1.40–1.82 (m, 4H, CH$_2$(1' and 2')); 1.88 (td, J = 13 and 4.5, 1H, Hax-C(5)); 3.75 (td, J = 13 and 2, 1H, Hax-C(6)); 4.04 (ddd, J = 13, 4.5, and 2, 1H, Heq-C(6)); 4.80 (dd, J = 7 and 5, 1H, H-C(2)). |
| 4,4-dimethyl-2-(1-methyl-butyl)1,3-oxathiane | terpeny, woody, black-currant, grapefruit | 1-methyl-pentanal | MS: 202(M$^+$, 8), 131(100), 87(8), 74(8), 69(88), 59(12), 55(12), 41(32) |
| 2-(2,4,4-trimethyl-1,3-oxa-thiane-2-yl)-acetamide | sulfury, herbal, hop, beer | 3-oxobutana-mide | MS: 203(M$^+$, 18), 145(309), 117(10), 102(100), 87(28), 85(35), 74(33), 69(65), 59(55), 56(32), 43(28), 41(48), 39(16) |

EXAMPLE 2

A citrus-herbaceous cologne for men was prepared by admixing the following ingredients:

| Ingredients | Parts by weight |
|---|---|
| Linalyl acetate | 130 |
| Isobornyl acetate | 70 |
| Ethyl acetoacetate | 10 |
| Ambrox ®[1] | 10 |
| 10%* Indol | 10 |
| Iso E Super[2] | 600 |
| 10%* Isobutylquinoleine[2] | 70 |
| Spearmint essential oil | 20 |
| Artemisia essential oil | 60 |
| 1,2,3,5,6,7-Hexahydro-1,1,2,3,3-pentamethyl-4-indenone | 30 |
| Sfuma lemon essential oil | 30 |
| 4-Cyclohexyl-2-methyl-2-butanol | 120 |
| Coumarin | 100 |
| Dihydromyrcenol | 540 |
| Eugenol | 40 |
| Habanolide ®[3] | 260 |
| Hedione ® HC[4] | 200 |
| 10%* Crystal moss | 50 |
| Patchouli essential oil | 350 |

-continued

| Ingredients | Parts by weight |
|---|---|
| Pimento leaves essential oil | 50 |
| Tyrol pine essential oil | 40 |
| Rosemary essential oil | 30 |
| 10%* γ-Undecalactone | 20 |
| Vert de Lilas | 20 |
| Ylang extra | 20 |
| 10%* Zestover ®[5] | 110 |
| Total | 2990 |

*in dipropylene glycol (DIPG)
[1](−)-(8R)-8,12-epoxy-13,14,15,16-tetranorlabdane; origin: Firmenich SA, Geneva, Switzerland
[2]origin: IFF, USA
[3]pentadecenolide; origin: Firmenich SA, Geneva, Switzerland
[4]methyl dihydrojasmonate; origin: Firmenich SA, Geneva, Switzerland
[5]2,4-dimethyl-3-cyclohexen-1-carbaldehyde; origin: Firmenich SA, Geneva, Switzerland Addition of 10 parts by weight of 2-ethyl-4,4-dimethyl-1,3-oxathiane to the above-described cologne base imparted to the latter a very nice and natural herbaceous note, reinforcing the thujonic aspect of the composition.

EXAMPLE 3
Synthetic thyme

A base composition was prepared by admixing the following ingredients:

| Ingredients | Parts by weight |
|---|---|
| Borneol Cryst. | 150 |
| Camphor | 100 |
| Carvacrol | 450 |
| α-Pinene | 100 |
| Pure citral | 20 |
| Eucalyptol | 100 |
| Distilled limonene | 90 |
| Linalol | 500 |
| Myrcene | 120 |
| Linalool oxide | 20 |
| Paracymene | 2000 |
| Caryophyllene | 80 |
| Pulegone | 20 |
| γ-Terpinene | 350 |
| α-Terpineol | 100 |
| Thymol | 50 |
| Total | 4250 |

Addition of 50 parts by weight of 2-ethyl-4,4-dimethyl-1,3-oxathiane to the above-described base composition imparted to the latter a distinct savory, thyme leaves effect, very natural, thus rendering the overall fragrance less terpenic-essence and less chemical.

EXAMPLE 4
Clary-sage Type Composition

A reconstitution of clary-sage was obtained by admixing the following ingredients:

| Ingredients | Parts by weight |
|---|---|
| Geranyl acetate | 20 |
| Linalyl acetate | 610 |
| Neryl acetate | 10 |
| Ambrox ®[1] | 10 |
| Caryophyllene | 20 |
| (E,E)-5-isopropyl-2-methyl-8-methylene-1,6-cyclodecadiene[2] | 50 |
| Linalol | 130 |
| Nerol | 5 |

-continued

| Ingredients | Parts by weight |
|---|---|
| Ocimene | 10 |
| Sclareol | 35 |
| Linalyl formate | 5 |
| Geraniol | 15 |
| α-Terpineol | 20 |
| α-Copaene[3] | 10 |
| Total | 950 |

[1](−)-(8R)-8,12-epoxy-13,14,15,16-Tetranorlabdane; origin Firmenich SA, Geneva, Switzerland
[2]origin: Firmenich SA, Geneva, Switzerland
[3](−)-(1R,2S,6S,7S,8S)-8-isopropyl-1,3-dimethyl-tricyclo[4.4.0.0.(2,7)]dec-3-ene; origin: Fluka Addition of 50 parts by weight of 2-(2,4-dimethyl-3-cyclohexene-1-yl)-4,4-dimethyl-1,3-oxathiane (IV) to the above-described clary-sage reconstitution gives to the latter a green-herbaceous, tagete direction, connotation, which is more fruity, more natural and more vivid than in the reconstitution without (IV).

EXAMPLE 5
Aromatic Shampoo With A Fresh Connotation

A base composition was prepared by admixing the following ingredients:

| Ingredients | Parts by weight |
|---|---|
| Isobornyl acetate | 50 |
| Benzyl acetate | 65 |
| 10%* cis-3-Hexenol acetate | 70 |
| Citronellyl acetate | 35 |
| Nopyl acetate | 50 |
| Hexylcinnamic aldehyde | 200 |
| 10%* Undecylenic aldehyde | 10 |
| 10%* γ-Undecalactone | 10 |
| Synthetic bergamot | 100 |
| Eugenol | 35 |
| Geraniol | 20 |
| Habanolide ®[1] | 40 |
| Hedione[2] | 280 |
| Helional | 30 |
| Lilial ®[3] | 140 |
| Linalool | 300 |
| Lyral ®[4] | 50 |
| Cyclosal | 20 |
| 10%* Crystal moss | 15 |
| Brazil sweet orange essential oil | 95 |
| laevo-Carvone | 330 |
| cis-3-Hexenol salicylate | 100 |
| Pure citral | 5 |
| Citronellol | 50 |
| 10%* Allyl cyclohexylpropionate | 25 |
| Brazil mint essential oil | 200 |
| Eucalyptol | 60 |
| Borneol | 40 |
| Camphor | 150 |
| 2-Phenyl-1-ethanol | 60 |
| 10%* cis-3-Hexenol | 30 |
| Terpineol ord. | 90 |
| Triplal[4] | 65 |
| 10%* Vanilline | 50 |
| Vert de lilas | 10 |
| Ylang essential oil | 20 |
| Total | 2900 |

*in DIPG
[1]pentadecenolide; origin: Firmenich SA, Geneva, Switzerland
[2]methyl dihydrojasmonate; origin: Firmenich SA, Geneva, Switzerland
[3]origin: Givaudan, Vernier, Switzerland
[4]origin: IFF, USA When 100 parts by weight of 2-(2,4-dimethyl-3-cyclohexene-1-yl)-4,4-dimethyl-1,3-oxathiane (10% in DIPG) were added to the above-described base composition, the latter acquired radiance, diffusion and natural character similar to that which can be obtained by addition of crushed mint leaves to the composition.

EXAMPLE 6

A green-herbaceous composition was prepared by admixing the following ingredients:

| Ingredients | Parts by weight |
| --- | --- |
| Hexylcinnamic aldehyde | 150 |
| 3-(4-Methoxyphenyl)-2-methylpropanal | 260 |
| Hedione ®[1)] | 300 |
| Mayol ®[2)] | 200 |
| Neobutenone ®[3)] | 10 |
| 10%* cis-2-Methyl-4-propyl-1,3-oxathiane | 15 |
| (±)-2,2,5-Trimethyl-5-pentyl-1-cyclopentanone | 15 |
| Total | 950 |

*in DIPG
[1)]methyl dihydrojasmonate; origin: Firmenich SA, Geneva, Switzerland
[2)]cis-7-p-menthanol; origin: Firmenich SA, Geneva, Switzerland
[3)]1-(5,5-dimethyl-1-cyclohexen-1-yl)-4-penten-1-one; origin: Firmenich SA, Geneva, Switzerland Addition of 50 parts by weight of 2-(2,4-dimethyl-3-cyclohexene-1-yl)-4,4-dimethyl-1,3–25 oxathiane (10% in DIPG) to the above-described composition imparted to the latter an unusual aromatic connotation reminiscent of the odor of chervil leaves.

EXAMPLE 7

A fruity, lactonic composition was prepared by admixing the following ingredients:

| Ingredients | Parts by weight |
| --- | --- |
| 10%* Amyl acetate | 20 |
| 10%* cis-3-Hexenol acetate | 30 |
| Styrallyl acetate | 10 |
| Terpenyl acetate | 300 |
| 10%* Ethyl-2-methylbutyrate | 10 |
| Undecalactone gamma | 30 |
| 10%* cis-3-Hexenol | 50 |
| Allyl cyclohexyl propionate | 10 |
| 0.1%* Ethylmaltol | 30 |
| Habanolide ®[1)] | 50 |
| α-Ionone | 10 |
| Phenoxy Isobutyrate | 50 |
| Hexyl isobutyrate | 20 |
| Hexyl acetate | 20 |
| 10%* Neobutenone ®[2)] | 10 |
| Florida orange essential oil | 130 |
| Verdyl propionate | 150 |
| γ-Nonalactone | 10 |
| Total | 940 |

*in DIPG
[1)]pentadecenolide; origin: Firmenich SA, Geneva, Switzerland
[2)]1-(5,5-dimethyl-1-cyclohexen-1-yl)-4-penten-l-one; origin: Firmenich SA, Geneva, Switzerland 50 Parts by weight of 2-(2,4-dimethyl-3-cyclohexene-1-yl)-4,4-dimethyl-1,3-oxathiane (10% in DIPG) were added to the above base composition. The new composition thus obtained possessed a fragrance with a green exotic aspect, reminiscent of the odor of mango peel.

What is claimed is:
1. A compound of formula

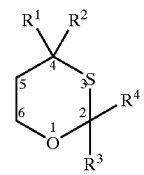

(I)

wherein $R^1$ and $R^2$ represent simultaneously or independently a linear or branched alkyl or alkenyl group containing 1 to 4 carbon atoms;
$R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and
$R^4$ represents a hydrogen atom or a linear alkyl group containing 1 to 4 carbon atoms, provided that 2-[2-(4-methoxyphenyl)ethenyl]-4,4-dimethyl-1,3-oxathiane, 4,4-dimethyl-2-(2-phenylethenyl)-1,3-oxathiane, 2,2,4,4-tetramethyl-1,3-oxathiane, 2,4,4-trimethyl-1,3-oxathiane, 4,4-dimethyl-1,3-oxathiane and 2-(2-methyl-1-propenyl)-4,4-dimethyl-1,3-oxathiane are excluded.

2. A compound according to claim 1, of formula

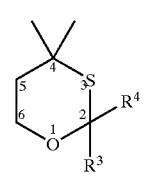

(II)

wherein $R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and
$R^4$ represents a hydrogen or a methyl group.

3. As a compound according to claim 2, 2-heptyl-4,4-dimethyl-1,3-oxathiane, 2-(5-methyl-2-furyl)-4,4-dimethyl-1,3-oxathiane, 4,4-dimethyl-2-propyl-1,3-oxathiane or 2,4,4-trimethyl-2-penthyl-1,3-oxathiane.

4. As a compound according to claim 2, 2-ethyl-4,4-dimethyl-1,3-oxathiane.

5. As a compound according to claim 2, 2-(2,4-dimethyl-3-cyclohexene-1-yl)-4,4-dimethyl-1,3-oxathiane.

6. A fine perfumery composition or fine perfumery product containing as active ingredient a compound according to claim 1.

7. A flavor preparation or flavor compostion containing as active ingredient a compound according to claim 1.

8. A method to confer, improve, enhance or modify the taste or flavor property of a flavor preparation or flavor composition which comprises adding thereto a flavor effective amount of a compound according to claim 1.

9. A method to confer, improve, enhance or modify the odor property of a fine perfumery composition or fine perfumery product, which comprises adding thereto a fragrance effective amount of a compound according to claim 1.

10. A functional perfumery composition or functional perfumery product or fine perfumery product containing as active ingredient a compound of formula I

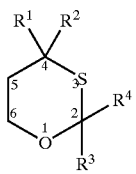

wherein $R_1$ and $R_2$ represent simultaneously or independently a linear or branched alkyl or alkenyl group containing 1 to 4 carbon atoms; $R_3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a carboxyl ester or amide group; and $R_4$ represents a hydrogen atom or a linear alkyl group containing 1 to 4 carbon atoms.

11. A perfuming composition or a perfumed product according to claim 10, characterized in that the active ingredient is a compound of formula

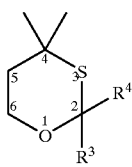

(II)

wherein $R^3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R^4$ represents a hydrogen or a methyl group.

12. A perfuming composition or a perfumed product according to claim 11, wherein the active ingredient is selected from the group consisting of 2-ethyl-4,4-dimethyl-1,3-oxathiane, 2-(2,4-dimethyl-3-cyclohexene-1-yl)-4,4-dimethyl-1,3-oxathiane, 2-heptyl-4,4-dimethyl-1,3-oxathiane, 2-(5-methyl-2-furyl)-4,4-dimethyl-1,3-oxathiane, 4,4-dimethyl-2-propyl-1,3-oxathiane and 2,4,4-trimethyl-2-penthyl-1,3-oxathiane.

13. A perfuming composition or a perfumed product according to claim 12, characterized in that the concentration of said active ingredient is comprised between 0.01% and 5%, and preferably from 0.02% and 3% by weight, with respect to the weight of the perfuming composition.

14. A perfuming composition or a perfumed product according to claim 11, in the form of a perfume or a cologne, a perfumed soap, a shower or bath gel, a shampoo, a body deodorant or antiperspirant, an ambient air deodorant, a liquid or solid detergent for textile treatment, a detergent composition or a cleaning product for dishes or varied surfaces, or a cosmetic preparation.

15. A flavored composition or a flavored product comprising a food or beverage and further comprising as active ingredient a compound of formula I

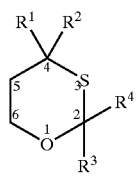

wherein $R_1$ and $R_2$ represent simultaneously or independently a linear or branched alkyl or alkenyl group containing 1 to 4 carbon atoms; $R_3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl, or alkenyl group containing 1 to 4 carbon atoms terminated by a carboxyl ester or amide group; and $R_4$ represents a hydrogen atom or a linear alkyl group containing 1 to 4 carbon atoms, wherein the active ingredient is present in a flavor effective amount.

16. A method to confer, improve, enhance or modify the odor property of a functional perfumery composition a functional perfumery product or a fine perfumery product which comprises adding thereto a fragrance effective amount of a compound of formula I

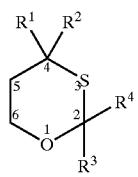

wherein $R_1$ and $R_2$ represent simultaneously or independently a linear or branched alkyl or alkenyl group containing 1 to 4 carbon atoms; $R_3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R_4$ represents a hydrogen atom or a liner alkyl group containing 1 to 4 carbon atoms.

17. A method to confer, improve, enhance or modify the taste or flavor property of a food or beverage composition which comprises adding thereto a flavor effective amount of a compound of formula I

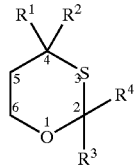

wherein $R_1$ and $R_2$ represent simultaneously or independently a, linear or branched alkyl or alkenyl group containing 1 to 4 carbon atoms; $R_3$ represents a hydrogen, a cycloalkyl or a cycloalkenyl group, possibly substituted, a furanyl group, possibly substituted, a linear or branched alkyl or alkenyl group containing 1 to 12 carbon atoms, possibly substituted, or a linear or branched alkyl or alkenyl group containing 1 to 4 carbon atoms terminated by a carboxyl ester or amide group; and $R_4$ represents a hydrogen atom or a linear alkyl group containing 1 to 4 carbon atoms.

* * * * *

UNITED STATES PATENT AND TRADEMARK OFFICE
CERTIFICATE OF CORRECTION

PATENT NO. : 6,559,109 B2
DATED : May 6, 2003
INVENTOR(S) : Lelandais

It is certified that error appears in the above-identified patent and that said Letters Patent is hereby corrected as shown below:

Column 16,
Line 58, change "compostion" to -- composition --.

Column 17,
Line 1, change "composition or functional" to -- composition, functional --;
Line 2, change "product or fine perfumery" to -- product, or a fine perfumery --; and
Line 19, after "or a" insert -- linear or branched alkyl or alkenyl group containing 1 to 4 carbon atoms terminated by a --.

Column 18,
Line 42, change "liner" to -- linear --; and
Line 56, change "a," to -- a --.

Signed and Sealed this

First Day of July, 2003

JAMES E. ROGAN
*Director of the United States Patent and Trademark Office*